(12) United States Patent
Stenlåås et al.

(10) Patent No.: US 10,495,569 B2
(45) Date of Patent: Dec. 3, 2019

(54) METHOD AND A SYSTEM FOR DETERMINING A COMPOSITION OF A GAS MIX IN A VEHICLE

(71) Applicant: Scania CV AB, Södertälje (SE)

(72) Inventors: Ola Stenlåås, Södertälje (SE); Henrik Röjdegård, Näsviken (SE)

(73) Assignee: Scania CV AB, Södertälje (SE)

( * ) Notice: Subject to any disclaimer, the term of this patent is extended or adjusted under 35 U.S.C. 154(b) by 11 days.

(21) Appl. No.: 15/576,473

(22) PCT Filed: Jun. 1, 2016

(86) PCT No.: PCT/SE2016/050512
§ 371 (c)(1),
(2) Date: Nov. 22, 2017

(87) PCT Pub. No.: WO2016/195580
PCT Pub. Date: Dec. 8, 2016

(65) Prior Publication Data
US 2018/0156724 A1    Jun. 7, 2018

(30) Foreign Application Priority Data
Jun. 5, 2015    (SE) ...................................... 1550736

(51) Int. Cl.
*G01N 21/3518*    (2014.01)
*G01N 33/22*    (2006.01)
*G01N 21/3504*    (2014.01)

(52) U.S. Cl.
CPC ..... *G01N 21/3518* (2013.01); *G01N 21/3504* (2013.01); *G01N 33/225* (2013.01)

(58) Field of Classification Search
CPC ........ G01N 21/31; G01N 21/35; G01N 21/39; G01N 21/359; G01N 21/3504;
(Continued)

(56) References Cited

U.S. PATENT DOCUMENTS 5,120,695 A    6/1992    Blumrich et al.
5,239,860 A    8/1993    Harris et al.
(Continued)

FOREIGN PATENT DOCUMENTS

CN    201513221 U    6/2010
CN    103442805    12/2013
(Continued)

OTHER PUBLICATIONS

International Search Report for PCT/SE2016/050512 dated Oct. 19, 2016.
(Continued)

*Primary Examiner* — Jamil Ahmed
(74) *Attorney, Agent, or Firm* — Moore & Van Allen PLLC; W. Kevin Ransom

(57) ABSTRACT

The invention relates to a method, system, and computer program product for determining a composition of a gas mix in a vehicle, said method comprising the steps of: exposing the gas mix with light; measuring data relating to a light absorption of the gas mix at at least two different pressures of the gas mix; and determining the composition of the gas mix based on said measured data. The invention relates also to a vehicle equipped with said system.

37 Claims, 5 Drawing Sheets

(58) Field of Classification Search
CPC ............ G01N 21/3518; G01N 33/225; G01N 33/0004; G01J 1/58; G01J 3/42
See application file for complete search history.

(56) References Cited

U.S. PATENT DOCUMENTS

| | | | |
|---|---|---|---|
| 7,559,194 B2 | 7/2009 | Westerberg | |
| 8,544,260 B2 | 10/2013 | Boorse et al. | |
| 9,573,097 B2 | 2/2017 | Reichinger et al. | |
| 9,670,855 B2 | 6/2017 | Dickson et al. | |
| 10,207,223 B2 | 2/2019 | Makino et al. | |
| 2004/0040289 A1 | 3/2004 | Mazur et al. | |
| 2004/0098979 A1 | 5/2004 | Hammerle et al. | |
| 2005/0069476 A1 | 3/2005 | Blakeman et al. | |
| 2005/0232830 A1 | 10/2005 | Bruck | |
| 2006/0039843 A1 | 2/2006 | Patchett et al. | |
| 2006/0092423 A1* | 5/2006 | Servaites ............ G01N 21/359 356/437 | |
| 2007/0150154 A1 | 6/2007 | Lenz | |
| 2008/0008629 A1 | 1/2008 | Doring et al. | |
| 2008/0060348 A1 | 3/2008 | Robel et al. | |
| 2009/0035194 A1 | 2/2009 | Robel et al. | |
| 2009/0035195 A1 | 2/2009 | Robel | |
| 2010/0024393 A1 | 2/2010 | Chi et al. | |
| 2010/0050604 A1 | 3/2010 | Hoard et al. | |
| 2010/0252737 A1* | 10/2010 | Fournel ............ G01J 3/02 250/338.4 | |
| 2010/0319320 A1 | 12/2010 | Mital et al. | |
| 2011/0052452 A1 | 3/2011 | Choi | |
| 2011/0085954 A1 | 4/2011 | Doring et al. | |
| 2011/0113759 A1 | 5/2011 | Tilinski et al. | |
| 2011/0211193 A1* | 9/2011 | Saveliev ............ G01N 21/3504 356/317 | |
| 2011/0271664 A1 | 11/2011 | Boorse et al. | |
| 2011/0295484 A1 | 12/2011 | L Henoret | |
| 2011/0313635 A1 | 12/2011 | Blanc et al. | |
| 2012/0117954 A1 | 5/2012 | Yasui et al. | |
| 2012/0255286 A1 | 10/2012 | Matsunaga et al. | |
| 2013/0078173 A1 | 3/2013 | Cox | |
| 2013/0091829 A1 | 4/2013 | Liljestrand et al. | |
| 2013/0202507 A1 | 8/2013 | Echoff et al. | |
| 2013/0232953 A1 | 9/2013 | Harmsen et al. | |
| 2013/0232958 A1 | 9/2013 | Ancimer et al. | |
| 2013/0289857 A1 | 10/2013 | Schmitt et al. | |
| 2013/0305695 A1 | 11/2013 | Henry et al. | |
| 2014/0052353 A1 | 2/2014 | Sujan et al. | |
| 2014/0056789 A1 | 2/2014 | Mussmann et al. | |
| 2014/0065044 A1 | 3/2014 | Ito et al. | |
| 2014/0229010 A1 | 8/2014 | Farquharson et al. | |
| 2015/0052878 A1 | 2/2015 | Qi | |
| 2015/0131093 A1 | 5/2015 | Saptari | |
| 2015/0143800 A1 | 5/2015 | Simon et al. | |
| 2015/0337702 A1 | 11/2015 | Ettireddy et al. | |
| 2016/0040616 A1 | 2/2016 | Dickson et al. | |
| 2016/0166990 A1 | 6/2016 | Phillips et al. | |
| 2017/0284919 A1* | 10/2017 | Slater ............ G01N 11/08 | |
| 2018/0221819 A1 | 8/2018 | Nilsson et al. | |

FOREIGN PATENT DOCUMENTS

| | | |
|---|---|---|
| DE | 3733501 A1 | 4/1989 |
| DE | 102006031650 A1 | 1/2008 |
| DE | 102008026191 A1 | 1/2009 |
| DE | 102009038835 A1 | 3/2011 |
| DE | 102010050312 A1 | 5/2012 |
| DE | 102012201809 A1 | 9/2012 |
| DE | 202013101028 U1 | 5/2013 |
| DE | 102015015260 A1 | 6/2017 |
| EP | 1181531 A1 | 2/2002 |
| EP | 2390480 A1 | 11/2011 |
| KR | 20140143145 A | 12/2014 |
| RU | 2354833 C2 | 6/2010 |
| RU | 2504668 C2 | 2/2017 |
| WO | WO0050974 A2 | 8/2000 |
| WO | 2007104382 A1 | 9/2007 |
| WO | 2009017639 A1 | 2/2009 |
| WO | 2012037342 A1 | 3/2012 |
| WO | 2013022516 A1 | 2/2013 |
| WO | 2013095214 A1 | 6/2013 |
| WO | 2013100846 A1 | 7/2013 |
| WO | 2014016616 A1 | 1/2014 |
| WO | 2014149297 A1 | 9/2014 |

OTHER PUBLICATIONS

Written Opinion of the International Searching Authority for PCT/SE2016/050512 dated Oct. 19, 2016.
International Preliminary Report on Publication for International Application No. PCT/SE2016/050512 dated Jun. 15, 2017.
Botar-Jid, Claudiu Cristian (2007)—Selective catalytic reduction of nitrogen oxides with ammonia in forced unsteady state reactors—Case based reasoning and mathematical model simulation reasoning; Retrieved online from http:// urn.fi/URN:ISBN:978-952-214-469-0; p. 3, second paragraph.
NOx Controls; EPA/452/B-02-001 Section 4—Retrieved online on Jun. 5, 2015 from http://www.epa.gov/ttncatcl/dirl/cs4-2ch2.pdf; pp. 2-6, third paragraph.

* cited by examiner

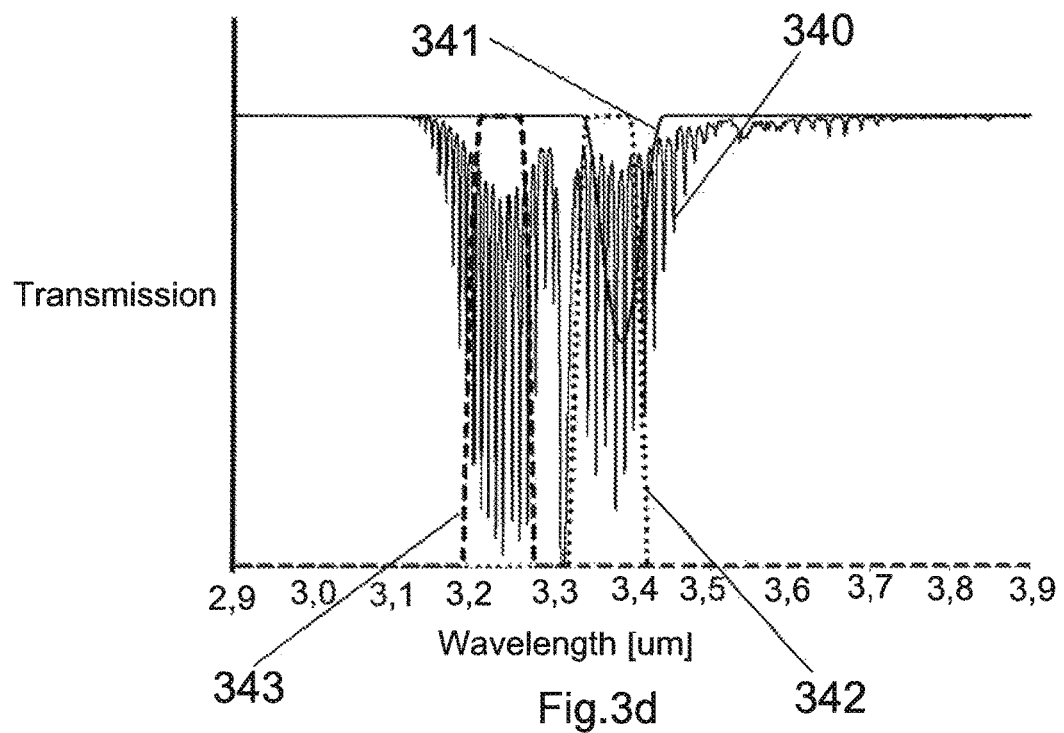
Fig.3d
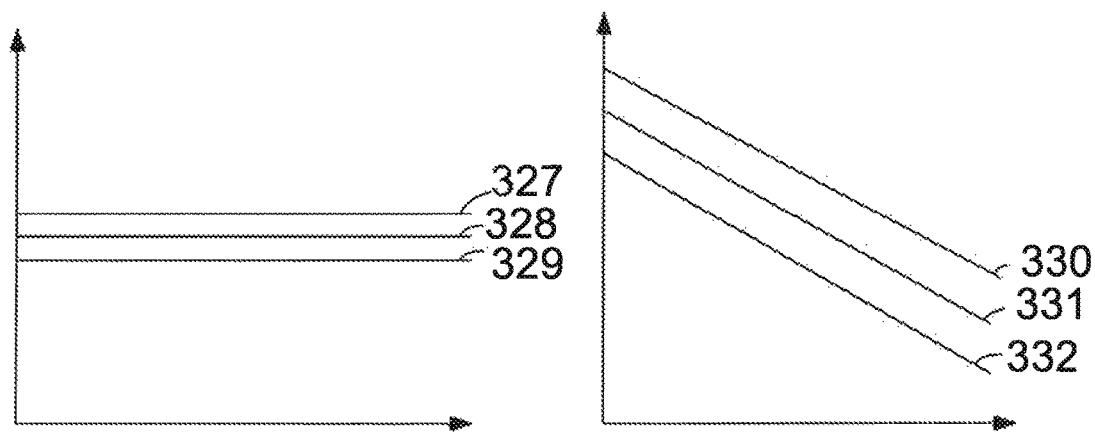
Fig.3e
Fig. 3f

METHOD AND A SYSTEM FOR DETERMINING A COMPOSITION OF A GAS MIX IN A VEHICLE

CROSS-REFERENCE TO RELATED APPLICATION(S)

This application is a national stage application (filed under 35 § U.S.C. 371) of PCT/SE2016/050512, filed Jun. 1, 2016 of the same title, which, in turn claims priority to Swedish Application No. 1550736-1, filed Jun. 5, 2015 of the same title; the contents of each of which are hereby incorporated by reference.

FIELD OF THE INVENTION

The present invention relates to a method for determining a composition of a gas mix in a vehicle. More particularly, the invention relates to a method determining a composition of a fuel gas mix in a vehicle having a combustion engine. The invention relates also to a computer program product comprising program code for a computer for implementing a method according to the invention. It relates also to a system determining a composition of a gas mix in a vehicle and a motor vehicle equipped with the system. More particularly, the invention relates to a system for determining a composition of a gas mix provided in a fuel container in a vehicle.

BACKGROUND OF THE INVENTION

Some vehicles of today are arranged to use a fuel gas or a fuel gas mix for generating an operational torque by means of a combustion engine. A fuel gas tank of such a vehicle may be refuelled manually at gas stations.

Examples of such a fuel gas can be natural gas, biogas, and town gas. Since a composition of such a fuel gas may vary depending on at which site said vehicle is refuelled e.g. proper engine operation may be difficult to optimize. In order to effectively, environmental friendly and safely operate said engine it is desired to determine a prevailing composition of said fuel gas. Examples of gas compositions of this fuel gas are methane, ethane, propane, butane, pentane, $N_2$, and $CO_2$. It is today difficult to accurately determine a prevailing composition of a gas mix of a fuel tank of a vehicle at a reasonable price.

SUMMARY OF THE INVENTION

An object of the present invention is to propose a novel and advantageous method for determining a composition of a gas mix in a vehicle.

Another object of the invention is to propose a novel and advantageous system and a novel and advantageous computer program for determining a composition of a gas mix in a vehicle.

An object of the present invention is to propose a novel and advantageous method for accurately determining a composition of a gas mix in a vehicle in a cost efficient way.

Another object of the invention is to propose a novel and advantageous system and a novel and advantageous computer program for accurately determining a composition of a gas mix in a vehicle in a cost efficient way.

Yet another object of the invention is to propose a method, a system and a computer program achieving a reliable, automated and time efficient determination of a fuel gas mix composition of a motor vehicle.

Yet another object of the invention is to propose an alternative method, an alternative system and an alternative computer program for determining a composition of a gas mix in a vehicle.

Some of these objects are achieved with a method and/or a system for determining a composition of a gas mix in a vehicle according to the claims. Advantageous embodiments are depicted in the dependent claims. Substantially the same advantages of method steps of the innovative method hold true for corresponding means of the innovative system.

According to an aspect of the invention there is provided a method for determining a composition of a gas mix in a vehicle, said method comprising the steps of:
exposing the gas mix with light;
measuring data relating to a light absorption of the gas mix at at least two different pressures of the gas mix; and
determining the composition of the gas mix based on said measured data.

This provides a method which is easy to implement. The method requires only a low number of measurements and these measurements can be performed by cheap detectors. This adds thus only little cost to the vehicle, while still providing reliable results. Knowing the composition allows then to adjust other parameters of the vehicle or its component to that composition.

Said two different pressures of the gas mix may be any suitable pressure values. Said pressure values can be predetermined pressure values.

Said data relating to the light absorption of the gas mix may relate to an intensity of detected light. Measuring light intensities is an easy-to-perform and reliable technique. Further, detectors for performing this are available at low cost.

Said gas mix may be exposed to light from at least one light source, and wherein said detected light may relate to the light which originates from said at least one light source and which has not been absorbed by the gas mix. Having the light from a light source contributes to perform the measurement under constant conditions. This is, for example, due to the fact that a light spectrum of a light source will basically remain constant between one measurement and the next.

Data relating to a light absorption of the gas mix may be measured at at least three different pressures of the gas mix. Hereby it is assured that a curve derived from the measurement can be adjusted so that it will be placed through the origin. As a result, the method will automatically compensate for effects like ageing of components or the like. The method may comprise the step of performing a measurement for adapting the base light intensity. This measurement does not need to be performed at the gas mix. This measurement could be performed at a reference gas. This assures that a curve derived from the measurement of the gas mix will be placed through the origin. As a result, a compensation for effects like ageing of components or the like is achieved. A further advantage is that the measurement for adapting the base light intensity only has to be performed at longer time intervals. Said longer time intervals can for example be once a drive cycle, once a week, once a month, or once a year.

Said data relating to the light absorption may be measured for at least two different wavelength ranges. This allows additional refining of the measurement method. Different concentrations of the gas mix might be determined more accurate, while not requiring any different detectors.

Said at least two different wavelength ranges may be situated between wavelengths of 1-10 μm, preferably between wavelengths of 3-5 μm. These are wavelength ranges for which suitable light sources with a corresponding emissions spectrum exist. Further, common components of common gas mixes for vehicle gases are absorbing light at these wavelength range. Even further, suitable detectors exist for these wavelength ranges. Performing the method at these wavelength ranges thus allows using components already on the market, which minimizes further development costs.

A first wavelength range out of the at least two wavelength ranges may be chosen such that basically only methane will absorb light in that wavelength range, when methane is chosen from the set consisting out of methane, ethane, propane, butane, $N_2$ and $CO_2$. Methane is often a component with high concentration in gas mixes for vehicles. The other components are also common in gas mixes for vehicles. Choosing the wavelength range as stated above thus allows determining a concentration of methane with high certainty. Having knowledge of the concentration of methane with high certainty has the further effect of lowering the uncertainty for the composition of the other components in the gas mix.

A second wavelength range out of the at least two wavelength ranges may be chosen such that at least one gas out of the set consisting out of ethane, propane, butane, $N_2$ and $CO_2$ significantly absorbs light within said second wavelength range. This allows measuring said at least one gas with high certainty.

A third wavelength range out of the at least two wavelength ranges may be chosen in such a way that $CO_2$ significantly absorbs light within said third wavelength range. For some gas mixes, such as biogas, a concentration of $CO_2$ might vary drastically. Especially measuring $CO_2$ allows thus determining an important parameter of these gas mixes.

The step of determining the composition of the gas mix may comprise the step of determining an amount of methane, and an amount of at least one of ethane, propane, and butane. These are the most common components in the most common gas mixes for vehicles. Determining them thus often is enough adjust to determine physical properties of the gas mix with an acceptable accuracy.

The step of determining the composition may comprise the step of comparing said measured data with pre-determined data stored in a library. Said library may be provided in a memory of an electronic control unit of the vehicle. This allows comparing measurement results with reference measurements. The reference measurements might be performed with high accuracy, thus giving good values for the actual measurements when the method is performed. Further, comparing with pre-determined data allows low computational complexity and thus a cost-efficient performing of the method.

Said pre-determined data stored in the library may comprise information regarding the composition of a gas mix based on a partial pressure of a gas in the gas mix and a detection threshold and/or broadening of the spectrum of at least one detector used to measure said data relating to said light absorption. Saturation and/or broadening are usually unwanted effects of detectors, which, however, here can be utilized to get information regarding the composition of a gas mix.

Said pre-determined data stored in the library may comprise information regarding the composition of a gas mix based on a total pressure of the gas mix and a detection threshold and/or broadening of the spectrum of at least one detector used to measure said data relating to said light absorption. Saturation and/or broadening are usually unwanted effects of detectors, which, however, here can be utilized to get information regarding the composition of a gas mix.

The method may further comprise the step of determining a number of components which should be determined in said composition of the gas mix, wherein said number of components is at least two, and wherein the step of measuring data relating to light absorption of the gas mix is performed at a number of different pressures of the gas mix, wherein said number of different pressures of the gas mix is at least the number of components plus one. This facilitates avoiding unnecessary measurements. One might have prior knowledge of what kind of gas mix is provided or used. With this knowledge, one might do assumptions about what could be relevant components in the gas mix. It is then enough to measure only those components. The system can thus be adapted to avoid making measurements for components where one is relatively sure that they will not be contained in the gas mix. This can also lower the total number of measurements which should be performed. Said different pressures of the gas mix can be pre-determined different pressures of the gas mix.

The method may further comprise the step of measuring the temperature and the total pressure of the gas mix at or after the outlet of a storage tank from where the gas mix is provided to the vehicle, wherein said measured temperature and total pressure of the gas mix is used to determine a number of different pressures of the gas mix at which said data relating to light absorption of the gas mix is measured. This is a concrete example of how unnecessary measurements can be avoided.

According to an aspect of the invention there is provided a method for adjusting engine parameters and/or exhaust gas treatment parameters in a vehicle, the method comprising the steps of:

determining a composition of a gas mix in a vehicle according to what is depicted herein; and adjusting engine parameters and/or exhaust gas treatment parameters of the vehicle based on said determined composition.

This allows saving fuel and/or extending the life time of components in the engine.

The method may further comprise the step of calculating at least one quantity out of calorific value, Wobbe index, inflammability, knock resistance based on the determined composition of the gas mix, catalyst light off temperature and adjusting said engine parameters based on said calculated at least one quantity. The named quantities are convenient parameters for determining the properties of a gas mix which are important for adjusting the engine.

The method may comprise the step of confirming or limiting said determined composition of said gas mix on the basis of at least one parameter from among the group consisting of λ-value (Lambda value), prevailing $NO_x$-values of an exhaust gas system of the vehicle, pressure values of engine cylinders, prevailing exhaust gas temperature and engine auto ignition characteristics. By confirming validity of said determined composition of said gas mix on the basis of operation parameters during vehicle operation a check procedure is advantageously provided. Here, and in the whole document the expression λ-value relates to an air to fuel ratio relative a stoichiometric air to fuel ratio.

According to an aspect of the invention there is provided a system for determining a composition of a gas mix in a vehicle, said system comprising:

means for exposing the gas mix with light;

means for measuring data relating to a light absorption of the gas mix at at least two different pressures of the gas mix; and means for determining the composition of the gas mix based on said measured data.

At the system said data relating to the light absorption of the gas mix may relate to an intensity of detected light.

Said means for exposing the gas mix with light may comprise at least one light source which is arranged to expose the gas mix with light, and wherein said detected light relates to the light which originates from said at least one light source and which has not been absorbed by the gas mix.

The system may comprise means for measuring data relating to a light absorption of the gas mix at at least three different pressures of the gas mix.

The system may comprise means for performing a measurement for adapting the base light intensity.

Said means for measuring data relating to the light absorption of the gas mix may be arranged to measure the data relating to the light absorption for at least two different wavelength ranges.

At the system said at least two different wavelength ranges may be situated between wavelengths of 1-10 μm, preferably between wavelengths of 3-5 μm.

At the system a first wavelength range out of the at least two wavelength ranges may be chosen such that basically only methane will absorb light in that wavelength range, when methane is chosen from the set consisting out of methane, ethane, propane, butane, $N_2$ and $CO_2$.

At the system a second wavelength range out of the at least two wavelength ranges may be chosen such that at least one gas out of the set consisting out of ethane, propane, butane, $N_2$ and $CO_2$ significantly absorbs light within said second wavelength range.

At the system a third wavelength range out of the at least two wavelength ranges may be chosen in such a way that $CO_2$ significantly absorbs light within said third wavelength range.

At the system said means for determining the composition of the gas mix may be arranged to determine an amount of methane, and an amount of at least one of ethane, propane, and butane.

Said means for determining the composition of the gas mix may be arranged to compare said measured data with pre-determined data stored in a library.

At the system said pre-determined data stored in the library may comprise information regarding the composition of a gas mix based on a partial pressure of a gas in the gas mix and a detection threshold and/or broadening of the spectrum of at least one detector used to measure said data relating to said light absorption.

Said pre-determined data stored in the library may comprise information regarding the composition of a gas mix based on a total pressure of the gas mix and a detection threshold and/or broadening of the spectrum of at least one detector used to measure said data relating to said light absorption.

The system may further comprise means for determining a number of components which should be determined in said composition of the gas mix, wherein said number of components is at least two, and wherein said means for measuring data relating to light absorption of the gas mix are arranged to performed the measuring at a number of different pressures of the gas mix, wherein said number of different pressures of the gas mix is at least the number of components plus one.

The system may further comprise means for measuring the temperature and the total pressure of the gas mix at or after the outlet of a storage tank from where the gas mix is provided to the vehicle, wherein said measured temperature and total pressure of the gas mix is used to determine a number of different pressures of the gas mix at which said data relating to light absorption of the gas mix is measured.

The system may comprise means for confirming or limiting said determined composition of said gas mix on the basis of at least one parameter from among the group consisting of λ-value (Lambda value), prevailing $NO_x$-values of an exhaust gas system of the vehicle, pressure values of engine cylinders, prevailing exhaust gas temperature and engine auto ignition characteristics. By confirming validity of said determined composition of said gas mix on the basis of operation parameters during vehicle operation a check procedure is advantageously provided. Means for confirming or limiting said determined composition of said gas mix may comprise an electronic control unit.

According to an aspect of the invention there is provided a system for adjusting engine parameters in a vehicle comprising means for determining a composition of a gas mix according to what is depicted herein and means for adjusting engine parameters of the vehicle (100) based on said determined composition. The system may comprise means for calculating at least one quantity out of calorific value, Wobbe index, inflammability, knock resistance based on the determined composition of the gas mix, and adjusting said engine parameters based on said calculated at least one quantity.

According to an aspect of the invention there is provided a vehicle comprising a system according to what is presented herein. Said vehicle may be a motor vehicle. Said motor vehicle might comprise a combustion engine. Said vehicle may be any from among a truck, bus or passenger car. According to an embodiment the system is provided for a marine application or industrial application.

According to an aspect of the invention there is provided a computer program for determining a composition of a gas mix in a vehicle, wherein said computer program comprises program code for causing an electronic control unit or a computer connected to the electronic control unit to perform the steps according to the method claims recited herein, when run on said electronic control unit or said computer.

According to an aspect of the invention there is provided a computer program for determining a composition of a gas mix in a vehicle, wherein said computer program comprises program code stored on a computer-readable medium for causing an electronic control unit or a computer connected to the electronic control unit to perform the steps according to the method claims recited herein.

According to an aspect of the invention there is provided a computer program for determining a composition of a gas mix in a vehicle, wherein said computer program comprises program code stored on a computer-readable medium for causing an electronic control unit or a computer connected to the electronic control unit to perform the steps according to the method claims recited herein, when run on said electronic control unit or said computer.

According to an aspect of the invention there is provided a computer program product containing a program code stored on a computer-readable medium for performing method steps according to the method claims recited herein, when said computer program is run on an electronic control unit or a computer connected to the electronic control unit.

According to an aspect of the invention there is provided a computer program product containing a program code stored non-volatile on a computer-readable medium for performing method steps according to the method claims recited herein, when said computer program is run on an electronic control unit or a computer connected to the electronic control unit.

Further objects, advantages and novel features of the present invention will become apparent to one skilled in the art from the following details, and also by putting the invention into practice. Whereas the invention is described below, it should be noted that it is not confined to the specific details described. One skilled in the art having access to the teachings herein will recognise further applications, modifications and incorporations in other fields, which are within the scope of the invention.

BRIEF DESCRIPTION OF THE DRAWINGS

For fuller understanding of the present invention and its further objects and advantages, the detailed description set out below should be read in conjunction with the accompanying drawings, in which the same reference notations denote similar items in the various diagrams, and in which:

FIGS. 3a-f show schematic curves which can be measured in relation to determining a composition of a gas mix;

DETAILED DESCRIPTION OF THE INVENTION

Figure 1:
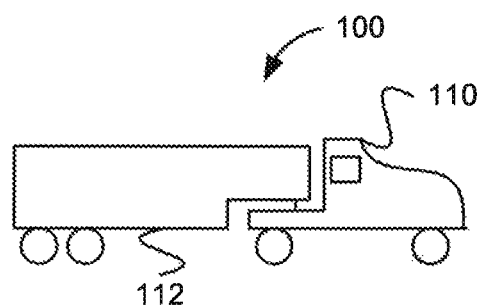
FIG. 1 schematically illustrates a vehicle according to an embodiment of the invention.

FIG. 1 depicts a side view of a vehicle 100. The exemplified vehicle 100 comprises a tractor unit 110 and a trailer 112. The vehicle 100 may be a heavy vehicle, e.g. a truck or a bus. It may alternatively be a car.

It should be noted that the inventive system for determining a composition of a gas in a vehicle is applicable to various vehicles, such as e.g. a mining machine, tractor, dumper, wheel loader, platform comprising an industrial robot, forest machine, earth mover, road construction vehicle, road planner, emergency vehicle or a tracked vehicle. The vehicle may according to an example be an autonomous vehicle.

It should be noted that the invention is suitable for application in various systems comprising a container holding a gas, or a liquid/solid transforming into gas before passing the sensor, for various purposes. It should be noted that the invention is suitable for application in any fuel gas powered engine system and is therefore not confined to combustion engines of motor vehicles. The innovative method and the innovative system in one aspect of the invention are well suited to other platforms which comprise a fuel gas powered engine system than motor vehicles, e.g. watercraft. The watercraft may be of any kind, e.g. motor boats, steamers, ferries or ships.

The innovative method may according to one aspect of the invention be applied to a pipeline configuration. Hereby a composition of a gas mix in said pipeline may be determined. Hereby information about said determined composition of a gas mix in said pipeline may be transmitted to a management station, or any other relevant party, by means of suitable transmitting means. Hereby a remote and distributed gas mix quality determination functionality may be provided at a pipeline configuration.

The innovative method and the innovative system may according to one aspect of the invention be applied at a fuel station, such as at a gas station. Hereby a composition of a gas mix (e.g. vehicle fuel) at said fuel station may be determined. Typically one or more large gas mix tanks are provided at said fuel station for allowing refuelling of a number of vehicles. This may be performed during or after fuelling a vehicle. Hereby information about said determined composition of an extracted gas mix from said large tanks may be transmitted to a management station, or any other relevant party, by means of suitable transmitting means. According to one example information about said determined composition of an extracted gas mix from said large tanks may be automatically transmitted to e.g. a hand held device of an operator of said vehicle by means of suitable transmitting means. Said hand held device may be a mobile phone. Hereby information about said determined composition of said gas mix provided to said vehicle may be automatically communicated to said operator and/or a control system of said vehicle. Said information may be utilized by said control unit so as to adjust engine parameters and/or exhaust gas treatment parameters of said vehicle.

The innovative method may according to one aspect of the invention be applied to a thermal power station or the like. Hereby a composition of a gas mix in said thermal power station may be determined. Hereby information about said determined composition of a gas mix in said thermal power station may be transmitted to a management station, or any other relevant party, by means of suitable transmitting means. Hereby a gas mix quality determination functionality may be provided at said thermal power station.

The innovative method and the innovative system according to one aspect of the invention are also well suited to, for example, systems which comprise industrial engines and/or engine-powered industrial robots.

The innovative method and the innovative system according to one aspect of the invention are also well suited to various kinds of power plants, e.g. an electric power plant which comprises an engine-powered generator.

The innovative method and the innovative system are also well suited to any engine system which comprises a fuel gas powered engine, e.g. on a locomotive or some other platform.

The innovative method and the innovative system are also well suited to any system which comprises a gas fuel powered $NO_x$ generator.

The term "link" refers herein to a communication link which may be a physical connection such as an optoelectronic communication line, or a non-physical connection such as a wireless connection, e.g. a radio link or microwave link.

The term "pipe" refers herein to a passage for holding and conveying a fluid, e.g. a fuel gas. The pipe may be a pipe of any desired size and be made of any suitable material, e.g. plastic, rubber or metal.

Other kinds of gases may of course be used. Methane, ethane, propane, butane, propane are herein cited as examples of a fuel gas mix, but one skilled in the art will appreciate that the innovative method and the innovative system are feasible with other types of fuel gas mixes, subject to necessary adaptations in control algorithms for executing program code in accordance with the innovative method.

Figure 2:
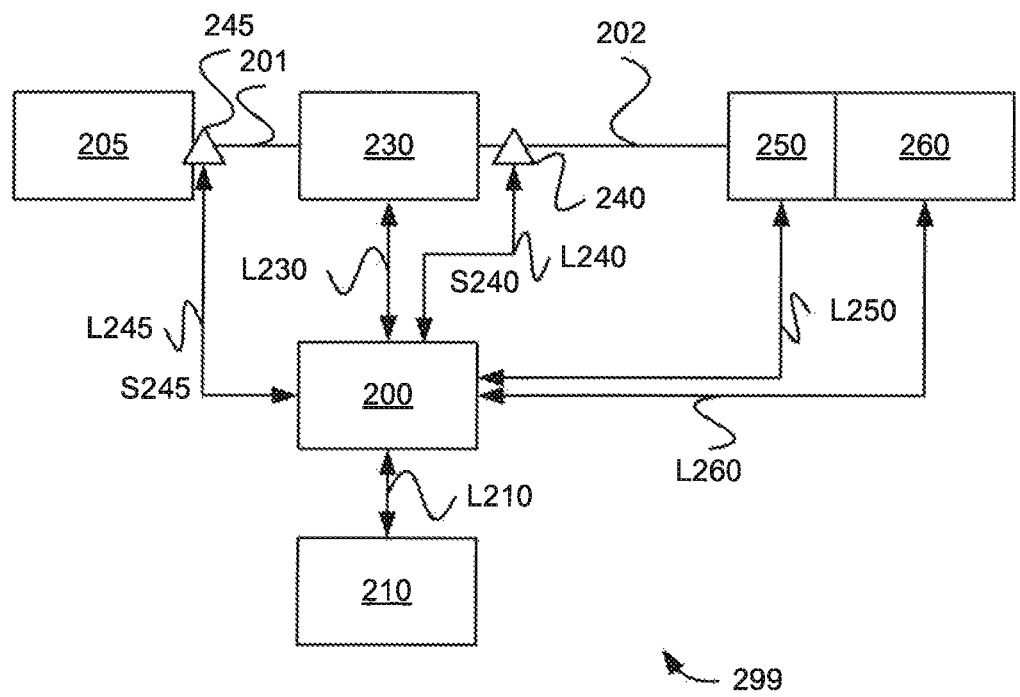
FIG. 2 schematically illustrates a subsystem for the vehicle depicted in FIG. 1, according to an embodiment of the invention.

FIG. 2 depicts a subsystem 299 of the vehicle 100. The subsystem 299 is situated in the tractor unit 110. It may be part of a fuel supply system. It comprises in this example a container 205 arranged to hold a fuel gas mix. The container 205 may alternatively be referred to as gas mix fuel tank or gas mix tank or fuel tank or storage tank. Said gas mix is pressurized within said container 205. The pressure of the gas mix of the container may be any suitable pressure, such as e.g. 5 bar, 20 bar, 50 bar, 100 bar, 200 bar or 300 bar. Said container 205 may be refuelled in any suitable manner, e.g. at a gas station. The subsystem 299 may comprise means (not shown) for detecting when said container has been refuelled, i.e. when additional gas (gas mix) has been provided into the container 205. Said detecting means may comprise a pressure sensor being provided in said container or any other suitable detecting means.

In one example, said container 205 is an external container. Said external container can, for example, be a storage tank at a gas station. In one example, said container 205 is a container containing a liquid which upon heating and/or pressure change makes a phase transition into its gaseous phase. An example of such a liquid is the so-called liquefied natural gas, LNG.

A first pipe 201 is arranged to convey said gas mix from said container 205 to a pressure management unit 230. Said pressure management unit 230 may comprise any suitable pressure means, such as a pressure regulator arrangement and/or one or more valve units. Said pressure management unit 230 is arranged to convey said gas mix to a second pipe 202 being provided downstream said pressure management unit 230. Said pressure management unit 230 is arranged to reduce a pressure of said gas mix downstream said pressure management unit 230. Hereby a pressure of said gas mix in said second pipe 202 may be controlled. Hereby said pressure of said gas mix in said second pipe 202 may be within a range of e.g. 1-20 bar, or 1-30 bar or 5-25 bar. Said pressure of said gas mix in said second line 202 may vary within any suitable pressure interval.

A first control unit 200 is arranged to control operation of said pressure management unit 230. Said first control unit 200 is arranged for communication with said pressure management unit 230 via a link L230. Hereby said first control unit 200 is arranged to control the pressure of said gas mix in said second pipe 202 by controlling operation of said pressure management unit 230.

Said second pipe 202 is arranged to convey said gas mix to a fuel supply arrangement 250. Said fuel supply arrangement 250 is arranged to provide said gas mix to combustion chambers of a combustion engine 260 of said vehicle 100. Said combustion engine 260 is arranged to generate an operational torque for propulsion of said vehicle 100 via a transmission (not shown).

Said first control unit 200 is arranged to control operation of said fuel supply arrangement 250. Said first control unit 200 is arranged for communication with said fuel supply arrangement 250 via a link L250. Hereby said first control unit 200 is arranged to control the operation of said fuel supply arrangement 250.

Said first control unit 200 is arranged to control operation of said combustion engine 260. Said first control unit 200 is arranged for communication with said combustion engine 260 via a link L260. Hereby said first control unit 200 is arranged to control the operation of said combustion engine 260.

A first sensor configuration 240 is provided at said second line 202 for exposing the gas mix with light and hereby measuring data relating to a light absorption of the gas mix at at least two different pressures of the gas mix. Said first sensor configuration 240 can comprise at least one light source. Said at least on light source can comprise light bulbs, and/or light emitting diodes, LED. However, even other light sources can be used. In one example said at least one light source is arranged to emit light in wavelength range of at least 1-10 µm, preferably at least 3-5 µm.

Said first sensor configuration can comprise at least one detector. Said at least one detector comprises in one example at least one non-dispersive infrared detector, NDIR-detector. Said first sensor configuration can comprise at least one optical filter. In one example, at least one detector is provided for every wavelength range which will be measured. This has the advantage that different wavelength ranges can be measured simultaneously. In one example, at least one optical filter is provided for every wavelength range which will be measured. In one example, at least two wavelength ranges are measured by the same detector. This can be achieved by providing an adaptable optical filter at said detector. The adaptable optical filter can change its transmission spectrum. This has the advantage that fewer components are needed.

In one example, light is emitted from said at least one light source, partially absorbed by the gas mix, transmitted through said at least one optical filter and impinging on said at least one detector. In one example, said at least one detector comprises a $CO_2$-sensor. Said first sensor configuration 240 is arranged for communication with said first control unit 200 via a link L240. Said first sensor configuration 240 is arranged to continuously or intermittently measuring data at a prevailing pressure of the gas mix in said second line 202 and send signals 5240 comprising said measured data to said first control unit via said link L240.

Herein said first control unit 200 is arranged to receive measured data from said first sensor configuration 240 relating to specific pressures of said gas mix in said second line 202. Hereby said first control unit 200 is arranged to determine the composition of the gas mix based on said measured data according to the invention.

A second sensor configuration 245 is in one example provided at an output of said container 205 for measuring a prevailing temperature and/or a prevailing pressure of the gas mix. Said second sensor configuration 245 is arranged for communication with said first control unit 200 via a link L245. Said second sensor configuration 245 is arranged to continuously or intermittently measuring data at a prevailing temperature of the gas mix at the output of said container 205 and send signals 5245 comprising said measured data to said first control unit via said link L245.

Said first control unit 200 is according to an example arranged to confirm validity of said determined composition of said gas mix on the basis of at least one parameter from among the group consisting of λ-value (Lambda value), prevailing $NO_x$-values of an exhaust gas system of the vehicle, pressure values of engine cylinders, prevailing exhaust gas temperature and engine auto ignition characteristics. Said parameters may be determined in any suitable way, e.g. by means of a Lambda sensor, $NO_x$-sensor, temperature sensor or adequate modelling/calculation.

Herein pressures of said gas mix may arise naturally in the system, such as during start of said system, during fuelling or during shut down of said vehicle. Hereby different pressures of the gas mix in said second pipe 202 arise naturally.

A second control unit 210 is arranged for communication with the first control unit 200 via a link L210 and may be detachably connected to it. It may be a control unit external to the vehicle 100. It may be adapted to conducting the innovative method steps according to the invention. The second control unit 210 may be arranged to perform the inventive method steps according to the invention. It may be used to cross-load software to the first control unit 200, particularly software for conducting the innovative method. It may alternatively be arranged for communication with the first control unit 200 via an internal network on board the vehicle. It may be adapted to performing substantially the same functions as the first control unit 200, such as measuring data relating to a light absorption of the gas mix at at least two different pressures of the gas mix and determining the composition of the gas mix based on said measured data. The innovative method may be conducted by the first control unit 200 or the second control unit 210, or by both of them.

Parts of the present invention can be illustrated with the help of FIG. 3*a-f*. The term determining a composition of a gas mix can relate to determining which different gases are part of the gas mix whose composition should be determined. Examples of gas mixes whose composition should be determined can be natural gas, biogas, and town gas. Examples of gas compositions of these gases are methane, ethane, propane, butane, pentane, $N_2$, and $CO_2$.

The term determining a composition of a gas mix relates in one example also to determining the concentration of the different gases. The concentration can, for example, be the molar concentration.

It should be understood that it often is not necessary to determine the whole composition of a gas mix. One might thus not be interested to know gasses only existing in, for example, a volume concentration of less than one percent, or less than one-tenth of a percent. This is due to the fact that gases with such low concentrations might not be especially relevant when determining properties of the gas mix such as calorific value, Wobbe index, inflammability, knock resistance, or the like. In one example, the composition of a gas mix is thus only determined for gases contributing up to a pre-determined value of the concentration. This pre-determined value can, for example, be 5%, 3%, 1%, 0.5%, or 0.1%.

In one example, only some components are determined in the composition of a gas mix. The term component refers to a pre-determined non-mixed gas. Examples of pre-determined non-mixed gases are methane, ethane, propane, butane, pentane, $N_2$, and $CO_2$.

Some of the gases said above are alkanes. The light absorption of an alkane, as well as an alkene or an alkyne is, to a large extent and as long as the number of coal atoms is not too high, proportional to the number of coal-hydrogen bonds. As an example, ethane can be defined to have a relative light absorption factor of 6. Propane, as the $C_3$ alkane will then roughly have a relative light absorption factor of 8, and butane, as the $C_4$ alkane will then roughly have a relative light absorption factor of 10, and so on. Similarly, propene as an example of an alkene will have a relative light absorption factor of 6. When restricting to the lower alkanes, alkenes, or alkynes, a higher number of coal-hydrogen bonds, will thus correspond to a higher absorption of light. It should be noted that even other hydrocarbons can be used in relation to the present disclosure, such as hydrocarbons with double bonds or triple bonds.

The concentration $C_x$ of a component x in a gas mix depends on the total concentration $C_{tot}$ of the gas mix and the fraction of that component x. The fraction of of a component x in a gas mix does not change with a change of the pressure, as long as no chemical reaction, no phase transition, and no radioactive processes happen. The total concentration $C_{tot}$ of the gas mix is according to the ideal gas law proportional to the total pressure $P_{tot}$ of the gas mix according to $C_{tot}=N/V=P_{tot}/(R \cdot T)$, where R denotes the ideal gas constant and T denotes the temperature of the gas. In that way, the measurement of a total concentration $C_{tot}$ of the gas mix can be replaced by a measurement of the total pressure $P_{tot}$ of the gas mix. In one example, the temperature T is measured as well. This can be done via a temperature sensor. In one example, the temperature T is basically constant between different measurements.

Given a certain gas mix, the light absorption of a component x in that gas mix is proportional to the concentration $C_x$ of said component x in the gas mix. The concentration $C_x$ of a component x in a gas mix is proportional to the partial pressure $P_x$ of said component x. As a consequence, the light absorption of a component in a gas mix is proportional to the partial pressure $P_x$ of said component x in the gas mix. Since the relation $P_x=P_{tot} \cdot \xi_x$ holds, the light absorption of a component x in a gas mix is in general also depending on the total pressure $P_{tot}$ of the gas mix. This is due to the fact that a higher total pressure of the gas mix leads to a higher number of gas molecules per volume and that higher number of gas molecules will then absorb more light.

The light absorption of the gas mix is also depending on the wavelengths of the light which is exposed to the gas mix. Thus, in one example the light absorption is depending on the emission spectrum of means for exposing the gas mix with light, such as a light source. A measured light absorption S will in general also depend on means for measuring data relating to a light absorption of the gas mix. Said means for measuring data relating to a light absorption of the gas mix can comprise one or more detectors. Said means for measuring data relating to a light absorption of the gas mix can also comprise one or more optical filters. The measured light absorption S will then depend on said one or more detectors and on said potential one or more optical filters. Said one or more optical filters can, for example, be used to transmit only certain wavelengths or certain wavelength ranges to the detector. Said one or more optical filter can be arranged to adjust the transmittance within its passband to enhance partial saturation effects used in the invention. Said partial saturation effect can related to a detection threshold γ which will be described in more detail later on. Said one or more detectors can, for example, have different sensitivities for different wavelengths. Detectors and optical filters can thus be chosen in such a way that wavelengths or wavelength ranges which are absorbed by the gas mix are transmitted to the detector and detected there. A gas mix consisting of three components will then show a measured light absorption $S=S_1+S_2+S_3$, where $S_1$, $S_2$, and $S_3$ denote the absorption of the first, second, and third component, respectively. In the following the principle will often be explained for a gas mix consisting of three components. It should, however, be understood that the above formula for S and the following formulas easily can be adapted with less or more terms for less or more components. At low enough concentrations, the absorption from a component x of the gas mix will be approximately linearly proportional to the concentration of that component. Thus, a measured light absorption $S_x$ for a component x will be proportional to $C_x$. For a gas mix with three components one can thus write $S_1=k_1 \cdot C_1=k_1 \cdot \xi_1 \cdot C_{tot}$, $S_2=k_2 \cdot C_2=k_2 \cdot \xi_2 \cdot C_{tot}$, and $S_3=k_3 \cdot C_3=k_3 \cdot C_{tot}$ with some, potentially different, factors $k_1$, $k_2$, and $k_3$. Since the total concentration $C_{tot}$ relates directly to the total pressure $P_{tot}$ as described above, and since the fraction relates directly to the partial pressure $P_x$ as described above, the measured light absorption S will in general depend on the partial pressure $P_x$ of the different components x of the gas mix, and the total pressure $P_{tot}$ of the gas mix. In other words, $S=S\ (P_x, P_{tot})$. It should be noted that $P_x$ denotes the partial pressure of each gas in the gas mix. Thus, in one example, $P_x=(P_{Me}, P_{Et}, P_{Pr}, P_{Bu}, P_{CO2} \ldots)$, where Me, Et, Pr, Bu are short hand notations of the first four alkanes. Relations arising from the so-called Lambert-Beer law are preferably applied in this relation.

Figure 3A:
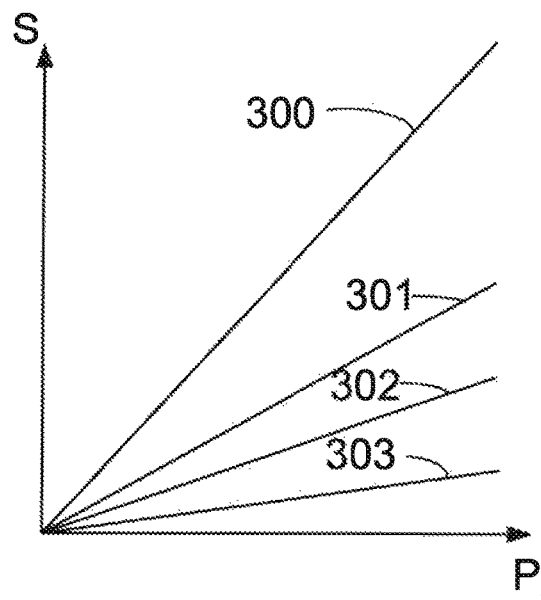

An example is given in FIG. 3a which shows schematic curves of a measurement. A measured light absorption S is plotted depending on a partial pressure $P_x$. In one example, the intensity of the light impinging on the detector is measured. This intensity is proportional to the transmission. The absorption is thus not necessarily measured directly. It is, however, known in the art how to deduct a value for the absorption from a value for the transmission. Even other quantities could be measured from which a value for the absorption can be deducted. The term measured light absorption S does thus not necessarily relate to a directly measured light absorption. The term measured light absorption relates in one example to an indirectly measured light absorption.

As an example, a first line 301 is a measured light absorption for methane depending on the partial pressure $P_{Me}$ of methane. A second line 302 can be a measured light absorption for ethane depending on the partial pressure $P_{Et}$ of ethane. A third line 303 can be a measured light absorption for propane depending on the partial pressure $P_{Me}$ of propane. A fourth line 300 can be a measured light absorption for a gas mix comprising methane, ethane, and propane depending on a total pressure $P_{tot}$.

Since one molecule of propane has a higher absorption than one molecule of ethane, and since one molecule of ethane has a higher absorption than one molecule of methane, the schematic FIG. 3a implies that the concentration of methane is substantially higher than the concentration of ethane, which in its turn is substantially higher than the concentration of propane. The signal for the gas mix, i.e. the fourth line 300, corresponds to the added signal for the different components, and potential further components.

It should be noted that the present disclosure does not demand measuring $P_{Me}$, $P_{Et}$, and $P_{Pr}$. In general, it will be enough to measure the signal for the gas mix to derive the composition of the gas mix. How this will work is described further in relation to FIGS. 3b and 3c.

Figure 3B:
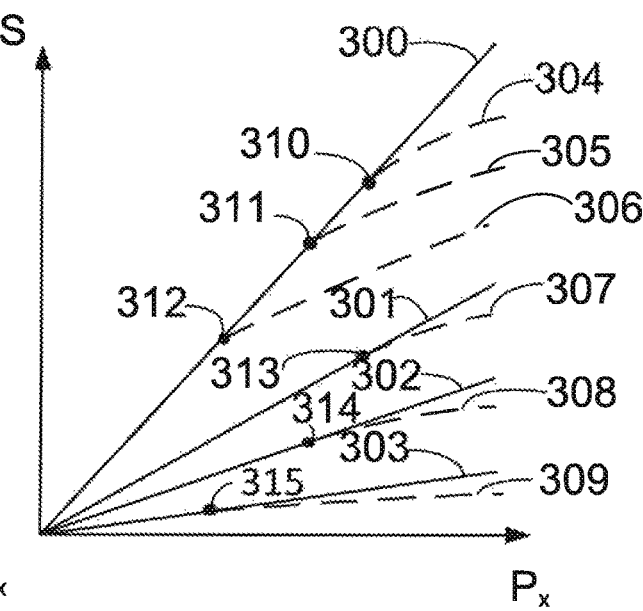

FIG. 3b shows schematic curves of a measurement. What is said about a measured light absorption S and a partial pressure $P_x$ in relation to FIG. 3a applies here as well. Further, the first, second, third and fourth lines 301, 302, 303, 304 from FIG. 3a are plotted in FIG. 3b as well.

It had turned out that the measured light absorption S also can depend on a detection threshold γ of a detector. In other words, $S=S\ (\gamma)$. When the measured light absorption reaches the detection threshold γ, a basically linear dependence of another quantity might no longer be basically linear. As an example, a basically linear dependence of the measured absorption S from a partial pressure $P_x$ might no longer be basically linear when the detection threshold γ is reached. This is indicated in FIG. 3b. In one example, $S=S\ (P_x, P_{tot}, \gamma)$. In one example, the detector will not respond at all to further changes in the concentration, i.e. in the partial pressure and thus the pressure, once the detection threshold γ is reached.

The discussed behavior of the detector can depend on the choice of a potential optical filter, for example on the transmission spectrum of the optical filter. The detection threshold γ can be reached at different concentrations $C_x$ and at different wavelengths for different components x.

In one example, when detecting the light absorption of methane, the basically linear dependence of the first line 301 on the partial pressure $P_{Me}$ might only be given until a first point 313, corresponding to a certain value of $P_{Me}$. After said first point 313, a second measured curve of methane 307 might show another behavior, preferably the second measured curve of methane 307 will bend downward.

In one example, when detecting the light absorption of ethane, the basically linear dependence of the second line 302 on the partial pressure $P_{Et}$ might only be given until a second point 314, corresponding to a certain value of $P_{Et}$. After said second point 314, a second measured curve of methane 308 might show another behavior, preferably the second measured curve of ethane 308 will bend downward.

In one example, when detecting the light absorption of propane, the basically linear dependence of the third line 303 on the partial pressure $P_{Pr}$, might only be given until a third point 315, corresponding to a certain value of $P_{Pr}$. After said third point 315, a second measured curve of propane 309 might show another behavior, preferably the second measured curve of propane 309 will bend downward.

It should be noted, that some curves might not show such a behavior, i.e. some curves might not have a detection threshold γ. As a result, the signal for the gas mix, for example the fourth line 300, might show a similar behavior. As an example, when the gas mix comprises methane, the measured light absorption for the gas mix will be basically linear until a first deviation point 310. This first deviation point 310 corresponds to a certain value of the total pressure of the gas mix. The first deviation point 310 corresponds further to a certain value of the partial pressure $P_{Me}$, of methane, as indicated by the first point 313. Thus, when realizing a non-linear behavior in the measured light absorption S of the gas mix starting from the first deviation point 310 one can conclude that the gas mix comprises methane. The measured light absorption S of the gas mix will then continue as a first deviation curve 304 after the first deviation point 310.

In the shown example, the corresponding would apply if the gas mix contains ethane or propane. In this case a second deviation point 311 and a third deviation point 312, respectively, will be present. The second deviation point 311 corresponds to a certain value of the partial pressure $P_{Et}$ of ethane, as indicated by the second point 314. The third deviation point 312 corresponds to a certain value of the partial pressure $P_{Pr}$, of propane, as indicated by the third point 315. Thus, when realizing a non-linear behavior in the measured light absorption S of the gas mix starting from the second deviation point 311 or the third deviation point 312, respectively, one can conclude that the gas mix comprises ethane or propane, respectively. The measured light absorption S of the gas mix will then continue as a second deviation curve 305 or a first deviation curve 306, respectively, after the second deviation point 311 or the third deviation point 312, respectively.

In the shown examples in FIG. 3b the gas mix reaches a detection threshold γ only for one component of the gas mix. It is, however, possible that the gas mix reaches a detection threshold γ for several components of the gas mix. This situation will be discussed in more detail in relation to FIG. 3c. As can be seen from FIG. 3b already, a detector reaches a detection threshold γ at different partial pressures for different gases. This corresponds then to different total pressures of the gas mix. Thus knowing the detection threshold γ behavior of a detector for the partial pressure of different gases allows to derive the composition of a gas mix if a corresponding detection threshold γ behavior is discovered in the measured light absorption S of the gas mix.

In one example, after the detection threshold γ is reached for the first component in the gas mix, the detector might show the behavior $S_1=k_1 \cdot \xi_1 \cdot C_{thresh,1}+k'_1 \cdot \xi_1 \cdot (C_{tot}-C_{thresh,1})$, $S_2=k_2 \cdot \xi_2 \cdot C_{tot}$, and $S_3=k_3 \cdot \xi_3 \cdot C_{tot}$, where $C_{thresh,1}$ denotes a threshold concentration for the first component above which the original basically linear behavior does not exist any longer, and $k'_1$ denotes a new factor, different from $k_1$. In general, a threshold concentrations $C_{thresh,x}$ depends on the component x. A threshold concentrations $C_{thresh,x}$ can also depend on the choice or design of a potential optical filter. A threshold concentrations $C_{thresh,x}$ can depend on the absorption spectrum of the gas. In one example, potential optical filters are chosen in such way as to increase separation of potential components of the gas. Thus, in one example, potential optical filters are chosen in such a way that the different pressures for which the detection threshold γ is reached for different components are not too close to each other, but do still occur regularly in common gas mixtures which might be analysed. It should be noticed that the curves 304-309 are only depicted schematically. The real form of these curves can differ depending on which detector is chosen and on which gas is detected. In one example, said curves 304-309 are basically linearly.

Thus, when determining one composition of a gas mix, it is enough to measure data relating to a light absorption of the gas mix at two or three different pressures of the gas mix.

In one example, two measurements are performed at relatively low pressures. In one example the expression relatively low pressure relates to values for the pressure where the detector has not reached the detection threshold γ yet. In the example of FIG. 3b this would correspond to two pressure values left of the pressure value given by the third deviation point 312.

Since it is expected that a measured line left of all deviation points is basically linear, said two pressure values will be enough to determine the slope of that line and an axis intercept of this line. In general, the axis interception of this line should be at the origin. In practice, however, deterioration of light sources, detectors, and possible other components might shift the line away from origin. Measuring the gas mix at at least two pressure values left of any deviation point thus allows correcting the signal for deterioration of components and possible other error sources.

In one example, it is enough to measure only one pressure values left of any deviation point. This is in one example the case when a determination of the base light intensity is provided in a different way. In one example, said different way relates to one or more measurements at other gases than the gas mix.

A second or a third measurement point is in one example measured at a relative high pressure value. The expression relatively high pressure value relates in one example to a pressure value where it is assumed that the detector will have reached the detection threshold γ for a gas component. In other words, said second or third measurement point is preferably chosen at the right of an expected deviation point. In general the form of a deviation curve 304-306 is known. Having a measured value for the light absorption S at pressure value right of a deviation point 310-312, this value will then be situated on one of the deviation curves 304-306. One can thus directly derive which component is present in the gas mix. As an example, if the second or third measurement point is on the first deviation curve 304, one can conclude that methane is a component of the gas mix. As another example, if the second or third measurement point is situated on the second deviation curve 305 or the third deviation curve 306, respectively, one can conclude that the ethane or propane, respectively, are a component of the gas mix.

In the example with the gas mix comprising three components, the measured light absorption S might be written as $S=S_1+S_2+S_3=k_1 \cdot \xi_1+k_2 \cdot k_3 \cdot \xi_3) \cdot C_{tot}-(C_{tot}-C_{thresh,1}) \cdot (k_1-k'_1) \cdot \xi_1$. Thus, when measuring S for at least two different pressure values, corresponding to two different values of $C_{tot}$, the concentration of $\xi_1$ can be directly derived. The factors and the threshold concentrations are generally known. In one example, they are known from reference measurements, such as of measurements stored in a library. Said reference measurements can be performed at a reference system. Said reference measurements can be performed in a laboratory. In one example, threshold concentrations $C_{thresh,x}$ are stored in a library as a function of pressure. Said pressure can be a total and/or a partial pressure. In one example, threshold concentrations $C_{thresh,x}$ are stored in a library as a function of gas component concentrations.

Figure 3C:
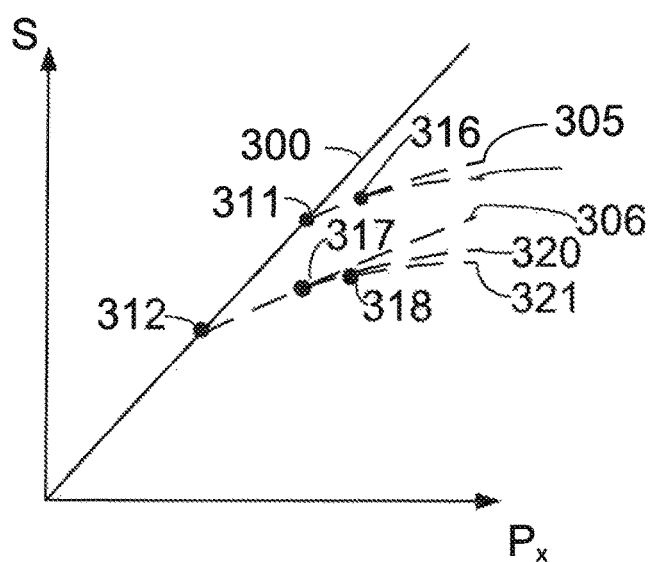

FIG. 3c shows schematic curves of a measurement. What is said about a measured light absorption S and a partial pressure $P_x$ in relation to FIG. 3a applies here as well. Further, elements with the same reference number as in FIG. 3a or FIG. 3b are the same elements. In one example, what has been described before in relation to these elements applies here as well.

In the shown example of FIG. 3b it has been explained how one component of a gas mix can be determined. Sometimes, one is interested in determining several components of a gas mix. FIG. 3c shows examples of how two or three components can be determined.

If a detector reaches the detection threshold γ for several of the components which are parts of the composition of a gas mix, not only one but several deviation points are present. In one example, a fourth deviation point 316 is present. In one example, a fifth deviation point 317 is present. In one example, a sixth deviation point 318 is present. The deviation curves after the fourth, fifth, and sixth deviation point 316-318 are denoted fourth deviation curve 319, fifth deviation curve 320 and sixth deviation curve 321, respectively.

In the example of FIG. 3c, the examples described in the following apply in addition to what has been described before. If at least parts of the fifth deviation curve 320 are detected, it can be concluded that ethane is comprised in the gas mix. If at least parts of the fourth deviation curve 319 or the sixth deviation curve 321 are measured it can be concluded that methane is comprised in the gas mix. If the fourth deviation curve 319 is measured it can be concluded that methane and ethane are comprised in the gas mix. If the fifth deviation curve 320 is measured it can be concluded that ethane and propane are comprised in the gas mix. If the sixth deviation curve 321 is measured it can be concluded that methane, ethane, and propane are comprised in the gas mix.

Preferably, values for the light absorption are measured for pressures values between all assumed deviation points. In the example of FIG. 3c, this results in that preferably at least two measurement points are measured left of the third deviation point 312, at least one measurement point is preferably measured between the third deviation point 312 and the second deviation point 311 or the fifth deviation point 317, respectively, at least one measurement point is preferably measured between the second deviation point 311 and the fourth deviation point 311, or between the fifth deviation point 317 and the sixth deviation point, respectively, and at least one measurement point is preferably measured to the right of the sixth deviation point 318. This allows determining which out of methane, ethane, and propane are comprised in the gas mix.

In an alternative example, only one measurement points is measured left of the third deviation point 312. The other measurement points are measured as described above. This is, for example, the case when a determination of the base light intensity is provided in a different way.

The above examples discussed the three components methane, ethane, and propane. It should, however, be understood that these are only examples and that this easily can be scaled to determine further components and/or other components in a gas mix.

In the general example of a gas mix with three components, factors $k'_2$ and $k'_3$, as well as thresholds $C_{thresh,2}$ and $C_{thresh,3}$ can be defined for the second and third component, respectively, in a way corresponding to what has been described for the first component in relation to FIG. 3b.

In one example, every new component requires at least one new measurement point. In one example, one component x can have an arbitrary number n of detection thresholds. One can then also have an arbitrary number of factors $k''_x$. In one example, a new measurement point is taken for each new factor $k''_x$.

The number of measurement points depends in one example on some prior knowledge of the gas mix. In one example, it is known which components potentially could be part of the gas mix. The number of measurement points can then be adapted to the potential components.

In one example, if prior knowledge exists that ethane, propane, and butane are comprised in the gas mix, the equation for the measured absorption can be written as $S=(k_{Et} \cdot \xi_{Et} \cdot k_{Pr} \cdot \xi_{Pr} \cdot k_{Bu} \cdot \xi_{Bu}) \cdot C_{tot}=(6/6 \cdot \xi_{Et} \cdot 8/6 \cdot \xi_{Pr}+10/6 \cdot \xi_{Bu}) k_{Et} \cdot C_{tot}$, where one uses the knowledge regarding the number of coal-hydrogen bonds as has been discussed before.

In one example, it is enough to determine a sum concentration of a combination of components. Thus, in one example a sum concentration of a combination of components of the gas mix is determined. For example, it might be enough to know the sum concentration of ethane, propane, and butane. In one example, this sum concentration is enough for controlling parameters of the vehicle. In one example, the sum concentration is a weighted sum concentration.

The present invention can even be used for higher hydrocarbons than those named explicitly here.

In one example, measuring the total pressure of the gas mix at or after the outlet of a storage tank from where the gas mix is provided to the vehicle can be used to get knowledge about partial pressures of the components in the gas mix. In one example, measuring the temperature of the gas mix at or after the outlet of a storage tank from where the gas mix is provided to the vehicle can be used to get knowledge about a maximal concentration of components in the gas mix. In one example, said knowledge about partial pressures and about a maximal concentration is knowledge about partial pressure and about a maximal concentration of propane and/or butane. In one example, said knowledge about partial pressures and about a maximal concentration is knowledge about partial pressure and about a maximal concentration of propane and/or butane in gas phase at a given temperature, pressure and gas mix. In one example, the expression "after the outlet" relates to any place, for example in a pipe, where the pressure and/or the temperature of the gas mix is representative to for the pressure and/or the temperature at the means for measuring data relating to a light absorption of the gas mix.

The present disclosure suggests measuring the gas mix at different pressures. This is in one example easily achieved by controlling a valve after an external storage tank of the gas mix when refuelling the vehicle. In another example, this is easily achieved by controlling a valve in the vehicle in combination with start and/or stop of an engine of the vehicle. At these occasions, controlling a valve for controlling the pressure in a measurement system will have no or only low impact on the driving experience of the vehicle.

Further improvements of the present disclosure are discussed in relation to FIG. 3d-3f. FIG. 3d shows schematic examples of transmission spectra. The horizontal axis shows a wavelength of the light. The vertical axis shows the normalized transmission. Line 340 shows a schematic example of a transmission spectrum of a gas mix which only contains methane. Line 341 shows a schematic example of a transmission spectrum of a gas mix which contains 15% of butane, where line 341 only relates to the absorption and transmission of butane in said gas mix. As can be seen in FIG. 3d, butane absorbs light basically only at wavelengths larger than 3.3 μm in the shown wavelength range. As can be seen in FIG. 3d, butane absorbs light basically only at wavelengths lower than 3.45 μm in the shown wavelength range.

As can be seen in FIG. 3d, methane absorbs light basically only at wavelengths larger than 3.1 μm in the shown wavelength range. As can be seen in FIG. 3d, methane absorbs light basically only at wavelengths lower than 3.8 μm in the shown wavelength range. As can be seen in FIG. 3d, methane absorbs a substantial amount of light at wavelengths below 3.3 μm in the shown wavelength range.

FIG. 3d shows a first transmission spectrum 342 of a first optical filter. FIG. 3e shows a second transmission spectrum 343 of a second optical filter. In one example said first and said second optical filters are different optical filters. In another example, said first and said second optical filter are the same optical filter. In one example, an optical filter is provided which can change its transmission spectrum. Examples of such optical filters are optical filters where the transmission spectrum is changed by an applied current to the optical filter, by tilting of the optical filter, by applying pressure to the optical filter, or by any other means.

If said second optical filter is used in between the gas mix and the detector, butane will not provide any signal. If a change in transmission is detected when using said second optical filter, this change is basically solely due to presence of methane. In one example, the detector averages over the wavelengths in the detected spectrum and supplies a single intensity value. With the help of the detector the amount of methane in the gas mix can then be derived. In one example, the partial pressure of the methane and/or total pressure of the gas mix is taken into account when deriving the amount of methane in the gas mix. In one example the detection threshold γ is taken into account when deriving the amount of methane in the gas mix. In one example the peaks in the ripple pattern of the transmission spectrum of a measured gas component are broadened. Such a broadening B leads to an increase of the Full width half maximum (FWHM) of the peaks. In one example the broadening B of the detected signal in the detector is taken into account when deriving the amount of methane in the gas mix. It should be understood that the broadening B can affect even other signals, such as the measured absorption of light S in relation to FIG. 3a-c. In other words, in one example S=S (B). Thus, in one example S=S ($P_x$, $P_{tot}$, γ, B).

FIG. 3e shows a schematic sketch of a measured averaged transmission, for example with an optical filter with said second transmission spectrum 343. The measured averaged transmission is shown on the vertical line. Thus, in the shown example the measured averaged transmission is affected by the amount of methane in the gas mix. This is due to the fact that only methane contributes to transmission changes when measured with said second optical filter 343. On the horizontal line, the percentage of butane in the gas mix is plotted. Line 327 shows a first percentage of methane in the gas mix, for example 60%. Line 328 shows a second percentage of methane in the gas mix, for example 70%. Line 329 shows a third percentage of methane in the gas mix, for example 80%. As can be seen, the averaged transmission for a given percentage of methane in the gas mix is not affected by the percentage of butane in the gas mix. On the other hand, by measuring the averaged transmission one can directly derive the amount of methane in the gas mix.

The first transmission spectrum 342 transmits changes in the transmission which can be caused by a change of the percentage of methane in the gas mix and/or by a change of the percentage of butane in the gas mix. However, due to the fact that the amount of methane in the gas mix can be determined with the help of an optical filter with said second transmission spectrum 343, this determined amount of methane can be used to derive how much of, for example, an averaged transmission signal after said first transmission spectrum 342 originates from said amount of methane. If the averaged signal after said first transmission spectrum 342 cannot be fully explained by the determined amount of methane, the difference between the expected averaged transmission from methane and the actually measured averaged transmission signal is caused by butane. Thus, said difference can be used to determine the amount of butane in the gas mix. An example is shown in FIG. 3f.

As in FIG. 3e, the horizontal line shows the averaged transmission and the vertical line shows the amount of butane in the gas mix. Line 330 shows a first percentage of methane in the gas mix, for example 60%. Line 331 shows a second percentage of methane in the gas mix, for example 70%. Line 332 shows a third percentage of methane in the gas mix, for example 80%. As can be seen, a measured averaged transmission for a given amount of methane depends on the amount of butane. Thus, by determining the amount of methane as described before and by measuring the averaged transmission with said first optical filter 342 one can derive the amount of butane.

Above, the principle has been described in relation to methane and butane. It should be understood that the principle easily can be scaled to more and/or other components in gas mix. As an example, one could use at least as much different transmission spectra of optical filters as there are components to be determined.

Figures 4A, 4B:
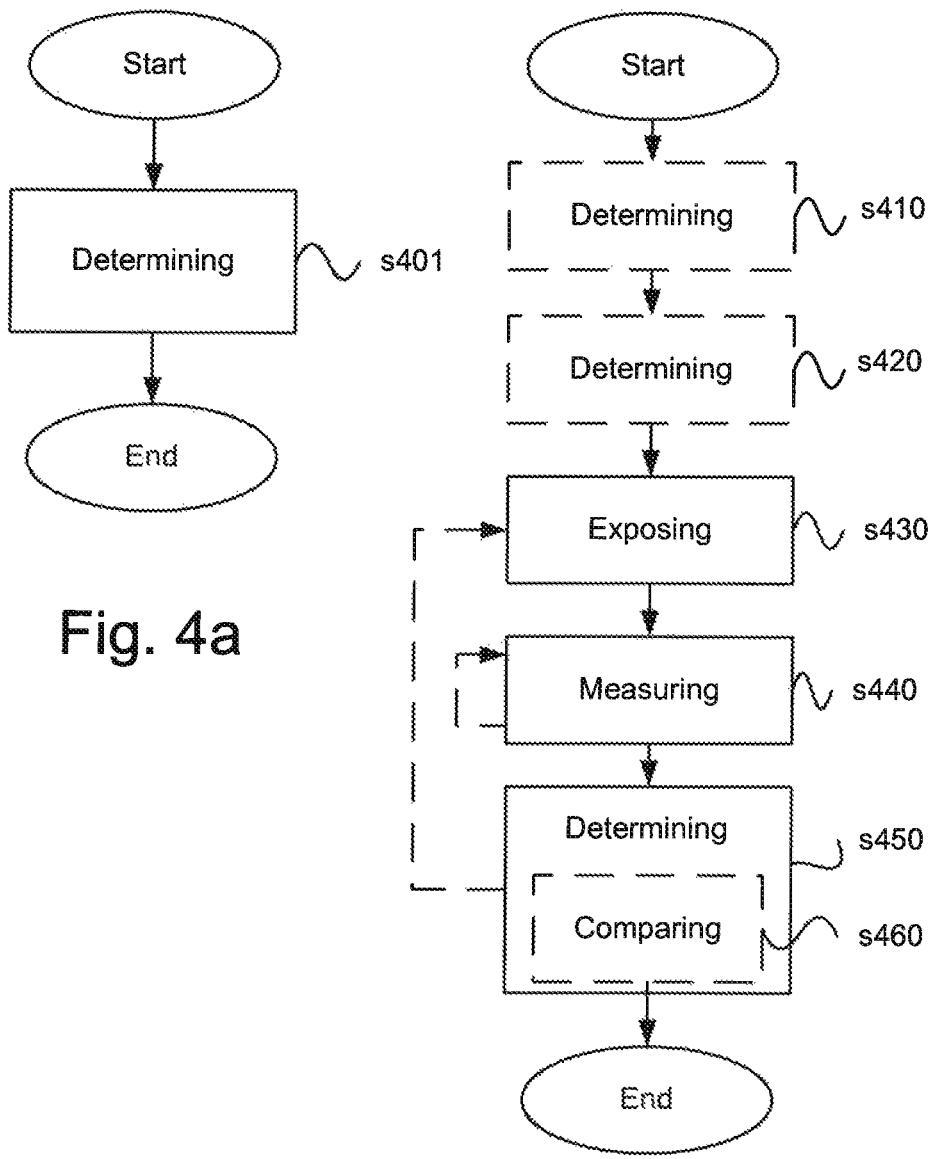
FIG. 4a is a schematic flowchart of a method according to an embodiment of the invention.
FIG. 4b is a more detailed schematic flowchart of a method according to an embodiment of the invention.

FIG. 4a schematically illustrates a flow chart of a method for determining a composition of a gas mix in a vehicle. The method comprises the method step s401. The method step s401 comprises the steps of:
  exposing the gas mix with light;
  measuring data relating to light absorption spectrum of the gas mix at at least two different pre-determined partial pressures of the gas; and
  determining the composition of the gas mix based on said measured data.

After the method step s401 the method ends.

FIG. 4b schematically illustrates a flow chart of a method for determining a composition of a gas mix in a vehicle. The method comprises in one example the method step s410.

The method step s410 comprises the step of measuring the temperature and the total pressure of the gas mix at or after the outlet of a storage tank 205 from where the gas mix is provided to the vehicle. Said measured temperature and total pressure of the gas mix is used to determine a number of different pressures of the gas mix at which said data relating to light absorption of the gas mix is measured. This step is preferably performed when the vehicle is fuelled or refuelled.

After the optional method step s410 a subsequent optional method step s420 is performed.

The optional method step s420 comprises the step of determining a number of components which should be determined in said composition of the gas mix. Said number of components is at least two. Step s440, which will be described later, will then be performed at a number of different pressures of the gas mix, wherein said number of different pressures of the gas mix is at least the number of components plus one. In one example, the determining is based on prior knowledge of the gas mix. The prior knowledge is in one example a set of possible components of the gas mix. In one example, the prior knowledge is a set of relevant components of the gas mix. This prior knowledge can, for example, be provided from a gas provider. This prior knowledge can also consist of any of the parameters discussed later on in relation to step s461. By using any of these parameters as prior knowledge the complexity of the analysis can be reduced.

After the optional method step s420 a subsequent method step s430 is performed.

The method step s430 comprises the step of exposing the gas mix with light. This is in one example done with at least one light source.

After the method step s430 a subsequent method step s440 is performed.

The method step s440 comprises the step of measuring data relating to a light absorption of the gas mix at at least two different pressures of the gas mix. The number of different pressures for mixing the gas mix is in one example determined in step s420. In one example, the number of different pressures for mixing the gas mix is pre-determined. This has been described in more detail in relation to FIG. 3a-f.

After the method step s440 a subsequent method step s450 is performed.

The method step s450 comprises the step of determining the composition of the gas mix based on said measured data. This has been described in more detail in relation to FIG. 3a-f.

In one example, the method returns to step s430. This can, for example, be the case when not the whole composition is determined yet. Then the method can continue by restarting at step s430 again for determining further components in the composition of the gas mix. In one example, the returning to step s430 comprises changing a filter spectrum.

If not returning to step s430, the method ends after step s450. The method can be restarted from the beginning.

In one example, step s450 comprises the additional step s460.

The method step s460 comprises comparing said measured data with pre-determined data stored in a library. Said library refers in one example to results from previous measurements and/or to simulation results. These results can be stored in a memory.

In one example, the method as described in relation to FIG. 4a and FIG. 4b is part of a method for adjusting engine parameters and/or exhaust gas treatment parameters in a vehicle. The method for adjusting engine parameters in a vehicle comprises the additional step of adjusting engine parameters and/or exhaust gas treatment parameters of the vehicle based on said determined composition. This is in one example done based on a calculated at least one quantity out of calorific value, Wobbe index, inflammability, knock resistance based on the determined composition of the gas mix and catalyst light off temperature. The described quantities are well known in the art.

The method step s460 may comprise the step s461 (not shown in the figures) of confirming or limiting said determined composition of said gas mix on the basis of at least one parameter from among the group consisting of λ-value (Lambda value), prevailing $NO_x$-values of an exhaust gas system of the vehicle, pressure values of engine cylinders, prevailing exhaust gas temperature and engine auto ignition characteristics. Hereby said determined composition of said gas mix may be evaluated on the basis of said operational parameters of said vehicle, such as engine operation parameters, emission system operation parameters, etc.

Many features of the methods described in relation to FIG. 4a and FIG. 4b are described in more detail in relation to FIG. 3a-f.

Figure 5:
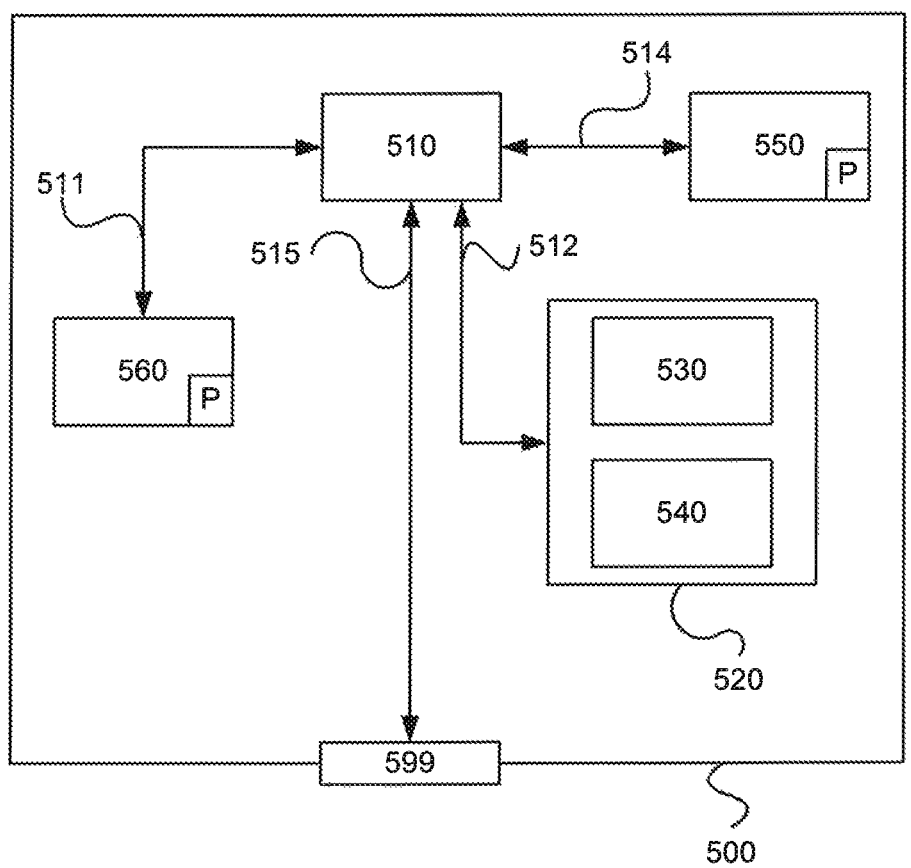
FIG. 5 schematically illustrates a computer according to an embodiment of the invention.

FIG. 5 is a diagram of one version of a device 500. The control units 200 and 210 described with reference to FIG. 2 may in one version comprise the device 500. The device 500 comprises a non-volatile memory 520, a data processing unit 510 and a read/write memory 550. The non-volatile memory 520 has a first memory element 530 in which a computer program, e.g. an operating system, is stored for controlling the function of the device 500. The device 500 further comprises a bus controller, a serial communication port, I/O means, an A/D converter, a time and date input and transfer unit, an event counter and an interruption controller (not depicted). The non-volatile memory 520 has also a second memory element 540.

The computer program comprises routines for determining a composition of a gas mix in a vehicle.

The computer program P may comprise routines for controlling an exposing process of said mix with light. This may be performed by means of said first control unit 200 controlling operation of said first sensor configuration 240.

The computer program P may comprise routines for measuring data relating to a light absorption of the gas mix at at least two different pressures of the gas mix. The computer program P may comprise routines for determining the composition of the gas mix based on said measured data. The computer program P may comprise routines for determining data relating to a light absorption of the gas mix at at least two different pressures of the gas mix. The computer program P may comprise routines for controlling a measurement for adapting the base light intensity.

The computer program P may comprise routines for determining the composition of the gas mix at any suitable predetermined pressure values.

The computer program P may comprise routines for controlling exposure of said gas mix to light from at least one light source, and wherein said detected light may relate to the light which originates from said at least one light source and which has not been absorbed by the gas mix.

The computer program P may comprise routines for controlling a measure process of said data relating to the light absorption for at least two different wavelength ranges.

Said at least two different wavelength ranges may be situated between wavelengths of 1-10 μm, preferably between wavelengths of 3-5 μm. Said at least two different wavelength ranges may be predetermined wavelength ranges. Said at least two different wavelength ranges may be stored in said non-volatile memory 520.

An operator may by means of any suitable user interface of said first control unit 200 chose a first wavelength range out of the at least two wavelength ranges may such that basically only methane will absorb light in that wavelength range, when methane is chosen from the set consisting out of methane, ethane, propane, butane, $N_2$ and $CO_2$.

An operator may by means of any suitable user interface of said first control unit 200 chose a second wavelength range out of the at least two wavelength ranges may such that at least one gas out of the set consisting out of ethane, propane, butane, $N_2$ and $CO_2$ significantly absorbs light within said second wavelength range.

An operator may by means of any suitable user interface of said first control unit 200 chose a third wavelength range out of the at least two wavelength ranges in such a way that $CO_2$ significantly absorbs light within said third wavelength range.

The computer program P may comprise routines for determining an amount of methane, and an amount of at least one of ethane, propane, and butane.

The computer program P may comprise routines for comparing said measured data with pre-determined data stored in a library. Said library may be provided in a memory of said first electronic control unit 200 of the vehicle 100.

Said pre-determined data stored in the library may comprise information regarding the composition of a gas mix based on a partial pressure of a gas in the gas mix and a detection threshold and/or broadening of the spectrum of at least one detector used to measure said data relating to said light absorption. Said pre-determined data may be stored in said non-volatile memory 520.

Said pre-determined data stored in the library may comprise information regarding the composition of a gas mix based on a total pressure of the gas mix and a detection threshold and/or broadening of the spectrum of at least one detector used to measure said data relating to said light absorption. Said pre-determined data may be stored in said non-volatile memory 520.

The computer program P may comprise routines for determining a number of components which should be determined in said composition of the gas mix, wherein said number of components is at least two, and routines for controlling a measure process regarding data relating to light absorption of the gas mix is performed at a number of different pressures of the gas mix, wherein said number of different pressures of the gas mix is at least the number of components plus one.

The computer program P may comprise routines for controlling a measuring process regarding the temperature and the total pressure of the gas mix at or after the outlet of a storage tank from where the gas mix is provided to the vehicle. The computer program P may comprise routines for determining a number of different pressures of the gas mix at which said data relating to light absorption of the gas mix is measured on the basis of said measured temperature and total pressure of the gas mix.

The computer program P may comprise routines for adjusting engine parameters and/or exhaust gas treatment parameters in a vehicle. The computer program P may comprise routines for determining a composition of a gas mix in a vehicle according to what is depicted herein. The computer program P may comprise routines for adjusting engine parameters and/or exhaust gas treatment parameters of the vehicle based on said determined composition.

The computer program P may comprise routines for calculating at least one quantity out of calorific value, Wobbe index, inflammability, knock resistance based on the determined composition of the gas mix, catalyst light off temperature and adjusting said engine parameters and/or exhaust gas treatment parameters based on said calculated at least one quantity.

The program P may be stored in an executable form or in compressed form in a memory 560 and/or in a read/write memory 550.

Where it is stated that the data processing unit 510 performs a certain function, it means that it conducts a certain part of the program which is stored in the memory 560 or a certain part of the program which is stored in the read/write memory 550.

The data processing device 510 can communicate with a data port 599 via a data bus 515. The non-volatile memory 520 is intended for communication with the data processing unit 510 via a data bus 512. The separate memory 560 is intended to communicate with the data processing unit via a data bus 511. The read/write memory 550 is arranged to communicate with the data processing unit 510 via a data bus 514. The links L210, L230, L240, L250, L260, for example, may be connected to the data port 599 (see FIG. 2).

When data are received on the data port 599, they are stored temporarily in the second memory element 540. When input data received have been temporarily stored, the data processing unit 510 will be prepared to conduct code execution as described above.

Parts of the methods herein described may be conducted by the device 500 by means of the data processing unit 510 which runs the program stored in the memory 560 or the read/write memory 550. When the device 500 runs the program, methods herein described are executed.

The foregoing description of the preferred embodiments of the present invention is provided for illustrative and descriptive purposes. It is not intended to be exhaustive, nor to limit the invention to the variants described. Many modifications and variations will obviously suggest themselves to one skilled in the art. The embodiments have been chosen and described in order to best explain the principles of the invention and their practical applications and thereby make it possible for one skilled in the art to understand the invention for different embodiments and with the various modifications appropriate to the intended use.

The invention claimed is:

1. A method for determining a composition of a gas mix in a vehicle, said method comprising the steps of:
    exposing said gas mix with light;
    measuring data relating to a light absorption of said gas mix at at least two different pressures of said gas mix;
    determining when said measured data relating to light absorption has reached a detection threshold at at least one of said pressures of said gas mix; and
    determining said composition of said gas mix based on said measured data, when said measured data has reached the detection threshold.

2. The method according to claim 1, wherein said data relating to the light absorption of said gas mix relates to an intensity of detected light.

3. The method according to claim 2, wherein said gas mix is exposed to light from at least one light source, and wherein said detected light relates to the light which originates from said at least one light source and which has not been absorbed by said gas mix.

4. The method according to claim 1, wherein data relating to a light absorption of said gas mix is measured at at least three different pressures of said gas mix.

5. The method according to claim 1, further comprising the step of performing a measurement for adapting the base light intensity.

6. The method according to claim 1, wherein the data relating to the light absorption is measured for at least two different wavelength ranges.

7. The method according to claim 6, wherein said at least two different wavelength ranges are situated between wavelengths of either 1-10 μm or 3-5 μm.

8. The method according to claim 6, wherein a first wavelength range out of the at least two wavelength ranges is chosen such that basically only methane will absorb light in that wavelength range, when methane is chosen from the set consisting out of methane, ethane, propane, butane, $N_2$ and $CO_2$.

9. The method according to claim 8, wherein a second wavelength range out of the at least two wavelength ranges is chosen such that at least one gas out of the set consisting out of ethane, propane, butane, $N_2$ and $CO_2$ significantly absorbs light within said second wavelength range.

10. The method according to claim 8, wherein a third wavelength range out of the at least two wavelength ranges is chosen in such a way that $CO_2$ significantly absorbs light within said third wavelength range.

11. The method according to claim 1, wherein the step of determining the composition of said gas mix comprises the step of determining an amount of methane, and an amount of at least one of ethane, propane, and butane.

12. The method according to claim 1, wherein the step of determining the composition comprises the step of comparing said measured data with pre-determined data stored in a library.

13. The method according to claim 12, wherein said pre-determined data stored in the library comprises information regarding the composition of a gas mix based on a partial pressure of a gas in said gas mix and a detection threshold and/or broadening of the spectrum of at least one detector used to measure said data relating to said light absorption.

14. The method according to claim 12, wherein said pre-determined data stored in the library comprises information regarding the composition of a gas mix based on a total pressure of said gas mix and a detection threshold and/or broadening of the spectrum of at least one detector used to measure said data relating to said light absorption.

15. The method according to claim 1, further comprising the step of determining a number of components which should be determined in said composition of said gas mix, wherein said number of components is at least two, and wherein the step of measuring data relating to light absorption of said gas mix is performed at a number of different pressures of said gas mix, wherein said number of different pressures of said gas mix is at least the number of components plus one.

16. The method according to claim 1, further comprising the step of measuring a temperature and a total pressure of said gas mix at or after the outlet of a storage tank from where said gas mix is provided to the vehicle, wherein said measured temperature and total pressure of said gas mix is used to determine a number of different pressures of said gas mix at which said data relating to light absorption of said gas mix is measured.

17. A method for adjusting engine parameters and/or exhaust gas treatment parameters in a vehicle based on a composition of a gas mix in the vehicle, the method comprising the steps of:
exposing said gas mix with light;
measuring data relating to a light absorption of said gas mix at at least two different pressures of said gas mix;
determining when whether said measured data relating to light absorption has reached a detection threshold at at least one of said pressures of said gas mix; and
determining said composition of said gas mix based on said measured data, when said measured data has reached the detection threshold; and
adjusting engine parameters of the vehicle based on said determined composition.

18. The method according to claim 17, further comprising the step of calculating at least one quantity out of calorific value, Wobbe index, inflammability, knock resistance based on the determined composition of said gas mix, catalyst light off temperature and adjusting said engine parameters and/or exhaust gas treatment parameters based on said calculated at least one quantity.

19. A system for determining a composition of a gas mix in a vehicle, said system comprising:
means for exposing said gas mix with light;
means for measuring data relating to a light absorption of said gas mix at at least two different pressures of said gas mix;
means for determining when said measured data relating to light absorption has reached a detection threshold at at least one of said pressures of said gas mix; and
means for determining a composition of said gas mix based on said measured data, when said measured data has reached the detection threshold.

20. The system according to claim 19, wherein said data relating to the light absorption of said gas mix relates to an intensity of detected light.

21. The system according to claim 19, wherein the means for exposing said gas mix with light comprise at least one light source which is arranged to expose said gas mix with light, and wherein said detected light relates to the light which originates from said at least one light source and which has not been absorbed by said gas mix.

22. The system according to claim 19, comprising means for measuring data relating to a light absorption of said gas mix at at least three different pressures of said gas mix.

23. The system according to claim 19 further comprising means for performing a measurement for adapting the base light intensity.

24. The system according to claim 19, wherein said means for measuring data relating to the light absorption of said gas mix are arranged to measure the data relating to the light absorption for at least two different wavelength ranges.

25. The system according to claim 24, wherein said at least two different wavelength ranges are situated between wavelengths of either 1-10 µm or 3-5 µm.

26. The system according to claim 24, wherein a first wavelength range out of the at least two wavelength ranges is chosen such that basically only methane will absorb light in that wavelength range, when methane is chosen from the set consisting out of methane, ethane, propane, butane, $N_2$ and $CO_2$.

27. The system according to claim 26, wherein a second wavelength range out of the at least two wavelength ranges is chosen such that at least one gas out of the set consisting out of ethane, propane, butane, $N_2$ and $CO_2$ significantly absorbs light within said second wavelength range.

28. The system according to claim 26, wherein a third wavelength range out of the at least two wavelength ranges is chosen in such a way that $CO_2$ significantly absorbs light within said third wavelength range.

29. The system according to claim 19, wherein said means for determining the composition of said gas mix are arranged to determine an amount of methane, and an amount of at least one of ethane, propane, and butane.

30. The system according to claim 19, wherein said means for determining the composition of said gas mix are arranged to compare said measured data with pre-determined data stored in a library.

31. The system according to claim 30, wherein said pre-determined data stored in the library comprises information regarding the composition of a gas mix based on a partial pressure of a gas in said gas mix and a detection threshold and/or broadening of the spectrum of at least one detector used to measure said data relating to said light absorption.

32. The system according to claim 30, wherein said pre-determined data stored in the library comprises information regarding the composition of a gas mix based on a total pressure of said gas mix and a detection threshold and/or broadening of the spectrum of at least one detector used to measure said data relating to said light absorption.

33. The system according to claim 19, further comprising means for determining a number of components which should be determined in said composition of said gas mix, wherein said number of components is at least two, and wherein said means for measuring data relating to light absorption of said gas mix are arranged to performed the measuring at a number of different pressures of said gas mix, wherein said number of different pressures of said gas mix is at least the number of components plus one.

34. The system according to claim 19, further comprising means for measuring a temperature and a total pressure of said gas mix at or after the outlet of a storage tank from where said gas mix is provided to the vehicle, wherein said measured temperature and total pressure of said gas mix is used to determine a number of different pressures of said gas mix at which said data relating to light absorption of said gas mix is measured.

35. A vehicle comprising a system for determining a composition of a gas mix in a vehicle, said system comprising:
means for exposing said gas mix with light;
means for measuring data relating to a light absorption of said gas mix at at least two different pressures of said gas mix;
means for determining when said measured data relating to light absorption has reached a detection threshold at at least one of said pressures of said gas mix; and
means for determining a composition of said gas mix based on said measured data, when said measured data has reached the detection threshold.

36. The vehicle according to claim 35, which vehicle is any from among a truck, bus or passenger car.

37. A computer program product containing a program code stored on a non-transitory computer-readable medium readable by a computer, said computer program product for determining a composition of a gas mix in a vehicle, said computer program code comprising computer instructions to cause one or more computer processors to perform the following operations:

exposing said gas mix with light;
measuring data relating to a light absorption of said gas mix at at least two different pressures of said gas mix;
determining when said measured data relating to light absorption has reached a detection threshold at at least one of said pressures of said gas mix; and
determining said composition of said gas mix based on said measured data, when said measured data has reached the detection threshold.

* * * * *

UNITED STATES PATENT AND TRADEMARK OFFICE
CERTIFICATE OF CORRECTION

PATENT NO. : 10,495,569 B2
APPLICATION NO. : 15/576473
DATED : December 3, 2019
INVENTOR(S) : Ola Stenlåås and Henrik Röjdegård Page 1 of 1

It is certified that error appears in the above-identified patent and that said Letters Patent is hereby corrected as shown below:

In the Claims

In Column 25, Claim 17, please change Line 11 to:
determining when said measured data relating to Signed and Sealed this
Eighteenth Day of February, 2020

Andrei Iancu
*Director of the United States Patent and Trademark Office*